United States Patent
Hayashi

[11] Patent Number: 6,151,518
[45] Date of Patent: Nov. 21, 2000

[54] INSTRUMENT FOR MEASURING CONCENTRATIONS OF CONSTITUENT PARTS OF BLOOD

[75] Inventor: Katsumi Hayashi, Kanagawa-ken, Japan

[73] Assignee: Fuji Photo Film Co., Ltd., Kanagawa-Ken, Japan

[21] Appl. No.: 09/261,214

[22] Filed: Mar. 3, 1999

[30] Foreign Application Priority Data

Mar. 3, 1998 [JP] Japan ................................. 10-050494

[51] Int. Cl.⁷ ............................................... A61B 5/00
[52] U.S. Cl. .......................................... 600/322; 600/330
[58] Field of Search ................................. 600/310, 322, 600/323, 326, 330

[56] References Cited

U.S. PATENT DOCUMENTS

| | | | |
|---|---|---|---|
| 5,706,821 | 1/1998 | Matcher et al. | 600/310 |
| 5,770,454 | 6/1998 | Essenpreis et al. | 600/322 |
| 5,983,121 | 11/1999 | Tsuchiya | 600/310 |

FOREIGN PATENT DOCUMENTS 53-26437  8/1978  Japan .

*Primary Examiner*—Eric F. Winakur
*Attorney, Agent, or Firm*—Sughrue, Mion, Zinn, Macpeak & Seas, PLLC

[57] ABSTRACT

A blood-constituent concentration measuring instrument capable of accurately measuring concentrations of the constituent parts of blood without invading tissue. Light source means (1) emits measuring light (S) to a living organism (2). The measuring light (S) consists of a plurality of wavelength components different from one another. Straight-advance light discrimination means (3) extracts a straight-advance light component or a scattered light component close thereto from light scattered at the living organism (2). Then, extinction-index change detection means (4) detects an extinction index change in straight-advance light component or the scattered light component extracted by the straight-advance light discrimination means (4). Calculation means (5) calculates concentrations of the constituent parts of the blood, based on the extinction index change for each wavelength component of the measuring light.

11 Claims, 9 Drawing Sheets

F I G. 9
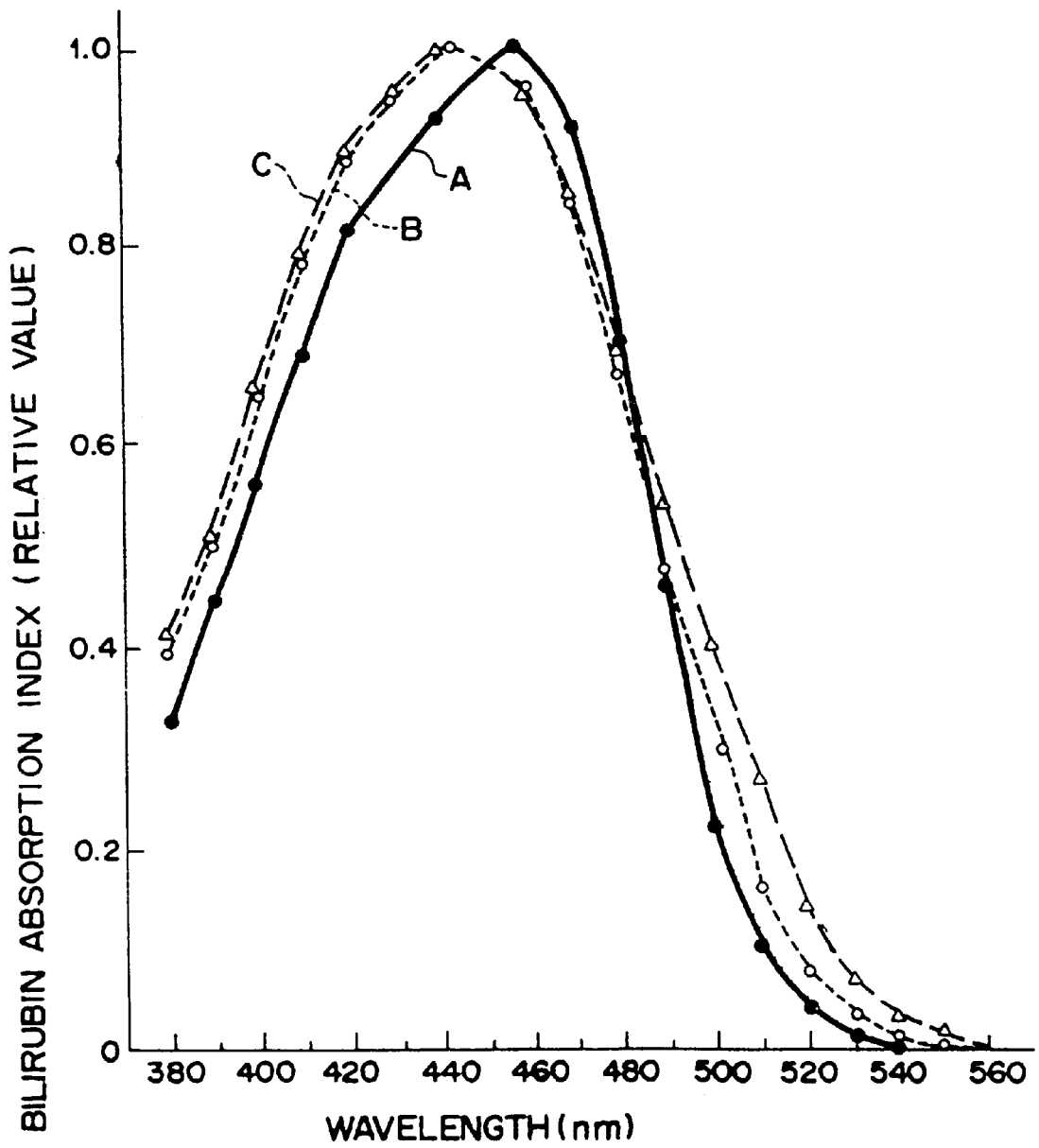

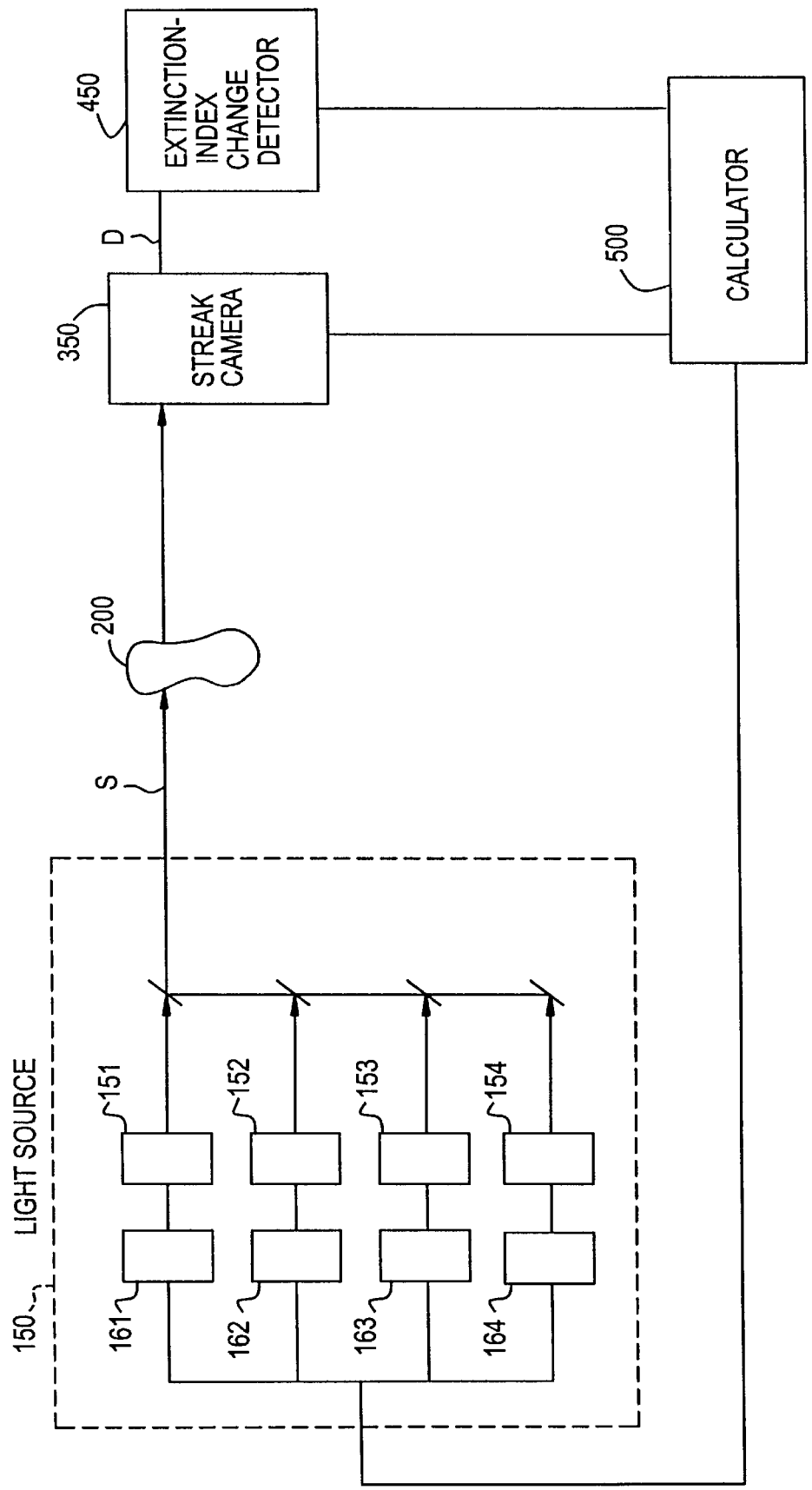

F I G . 11A
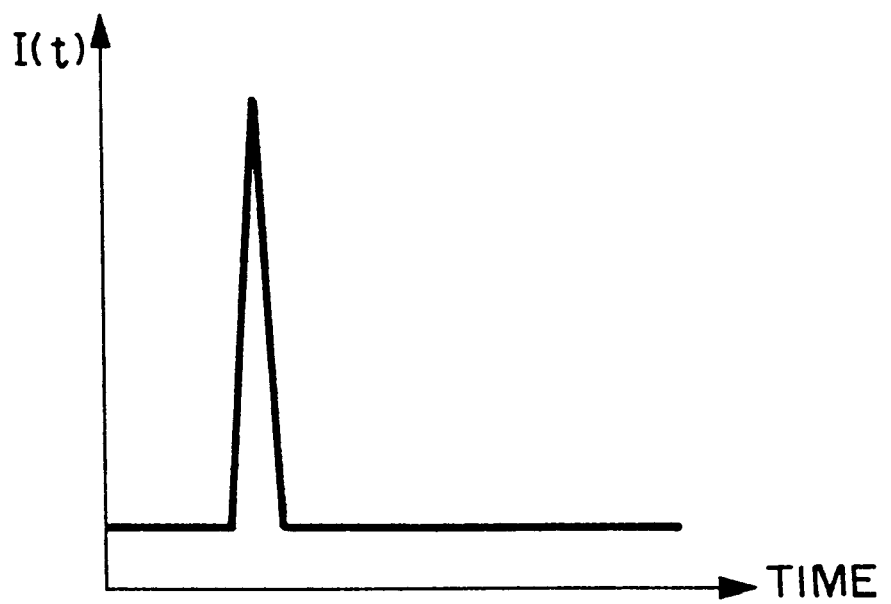
F I G . 11B
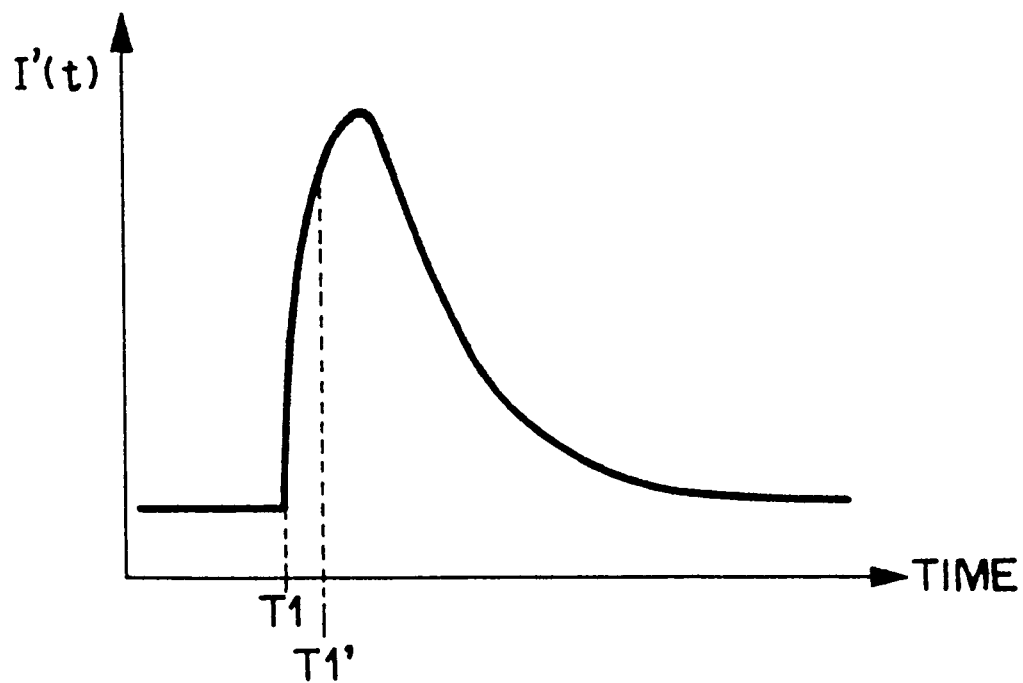

INSTRUMENT FOR MEASURING CONCENTRATIONS OF CONSTITUENT PARTS OF BLOOD

FIELD OF THE INVENTION

The present invention relates generally to a method and an instrument for optically measuring the concentration of the constituent parts of the blood of a living organism without invasion, and more particularly to a method and an instrument suitable for measuring the concentration of the hemoglobin (oxyhemoglobin, deoxyhemoglobin, carboxyhemoglobin, methemoglobin, etc.) in blood and the concentration of the bilirubin in blood.

DESCRIPTION OF THE RELATED ART

As is generally known, monitoring of the oxygen concentration of the tissue of a living organism has extremely great significance in clinical medicine. The oxygen dynamics evaluation method in the clinical medicine is roughly classified into oxygenation, oxygen supply, oxygen consumption, and oxygen supply-demand balance from the aspect of the movement of oxygen within a living organism.

The parameters relating to oxygenation and oxygen supply, among the above-mentioned classified items, are considered important. The reason for this is that oxygen is the most important substance for maintaining life activities and therefore if oxygen supply is cut off even for a very short time, the cellular tissue of a living organism will undergo a great damage. For this reason, during anesthesia when there is a possibility of the oxygen supply being unstable, or during intensive care of a patient with breathing deficiency or circulation deficiency, it becomes particularly important to monitor whether or not oxygen is being supplied appropriately.

The supply of oxygen to the tissue of a living organism is performed by arterial blood. Hence, it is conceivable to monitor the oxygen concentration in blood by measuring the concentrations of various kinds of hemoglobin in arterial blood in order to ascertain whether or not oxygen is being appropriately supplied to the tissue of a living organism.

On the other hand, it is known that if the bilirubin in blood is cumulated in the body of a newborn baby, it will cause jaundice. From this respect there is also a demand for accurately measuring the bilirubin concentration in blood in order to monitor for jaundice in newborn babies.

As an instrument for measuring the concentration of hemoglobin, bilirubin or the like in blood described above, the following instruments have hitherto been known.

Instrument for measuring hemoglobin concentrations in blood:

(1) Pulse oximeter (optical blood measuring instrument)

This instrument extracts an extinction index, based on a change in the extinction index caused by the pulsation of arterial blood, and measures the degree of oxygen saturation=oxyhemoglobin/(oxyhemoglobin+deoxyhemoglobin) from the extracted extinction index. Basically, the degree of oxygen saturation is calculated based on the regression line between the ratio of the extinction index changes in light of two wavelengths emitted to a living organism and the previously calculated degree of oxygen saturation in blood. This instrument has a characteristic in that it can easily make a measurement without invasion and is relatively inexpensive. For a detailed discussion on this instrument, see, for example, Japanese Patent Publication No. 53(1978)-26437.

(2) CO-oximeter

This instrument dissolves gathered blood and measures the absorption indices for a plurality of wavelengths within a cuvette, thereby calculating the absolute concentrations of various kinds of hemoglobin, such as oxyhemoglobin, deoxyhemoglobin, carboxyhemoglobin, methemoglobin and the like. This CO-oximeter has a characteristic in that it can calculate the oxygen content of blood as well as the degree of oxygenation of blood with a high degree of accuracy.

Instrument for measuring bilirubin concentration in blood:

(1) Instrument for measuring bilirubin concentration in serum

In this instrument, the blood gathered from the heel of the leg of a newborn baby with a surgical knife is put in a centrifugal separator to obtain serum, and the bilirubin concentration in the obtained serum is calculated. In the measurement of the bilirubin concentration in serum, a direct colorimetric method capable of making a measurement with a small quantity of serum is often adopted.

(2) Minolta jaundice meter

This instrument takes advantage of the fact that the optical concentration difference between light of wavelengths $\lambda 1$ and $\lambda 2$ different in the absorption coefficient of bilirubin has a correlation with bilirubin concentration, thereby detecting the degree of yellowish skin of a newborn baby as the optical concentration difference between blue and green wavelength regions without invasion. More specifically, blue light and green light are incident upon on the skin and absorbed on the side of a short wavelength by the bilirubin that has turned the subcutaneous fat yellow. Thereafter, the blue light and the green light are scattered and reflected and again emerge from the skin surface. Part of the emergent blue light and part of the emergent green light are detected to calculate the optical concentration difference therebetween.

The aforementioned 4 conventional instruments are admitted to have the following problems. First, the pulse oximeter of the aforementioned hemoglobin-concentration measuring instruments has the problem of measurement accuracy being low. That is, as previously described, this instrument measures the degree of oxygen saturation based on the regression line between the ratio of the extinction index changes in two wavelengths and the previously calculated degree of oxygen saturation in blood. However, the regression line and the degree of oxygen saturation do not match with each other over a wide range, because blood is a strong scattering medium. Hence, generally in the case where the degree of oxygen saturation is less than 70%, a measured value will depart considerably from the regression line.

In addition, the degree of oxygen saturation means the degree of oxygenation in blood=oxyhemoglobin/(oxyhemoglobin+deoxyhemoglobin) and shows the relative value of oxyhemoglobin. Therefore, the pulse oximeter cannot calculate the supply amount of oxygen in blood (oxygen content). Furthermore, this pulse oximeter is also admitted to have the problem that a measured value varies with a hematocrit value.

Next, the aforementioned CO-oximeter has the problem that the measuring operation becomes complicated, because it requires the dissolution of blood which is invasive.

On the other hand, as to the aforementioned instruments for measuring the bilirubin concentration in blood, the instrument for measuring the bilirubin concentration in serum has the problem that it cannot be frequently used, because it invades tissue.

The aforementioned Minolta jaundice meter has difficulty in that a measured value is not the concentration of bilirubin but a relative value corresponding to the bilirubin concentration. The correlation between the aforementioned optical concentration difference (which is this relative value) and the bilirubin concentration in serum varies considerably with birth weight. As a result, even in the case of the same bilirubin concentration in serum, sometimes a measured value is varied considerably by birth weight.

Furthermore, for the above-mentioned optical concentration difference, the correlation with the bilirubin in serum varies considerably with a portion to be measured, race, skin color and the like. As a result, even in the case of the same disease, there will arise a problem that a measured value will vary depending upon a portion to be measured or each individual and the like.

SUMMARY OF THE INVENTION

The present invention has been made in view of the problems found in the conventional instruments. Accordingly, it is an object of the present invention to provide a blood-constituent concentration measuring instrument that is capable of accurately measuring the concentrations of various constituent parts of blood, particularly the hemoglobin concentration in blood (e.g., oxyhemoglobin, deoxyhemoglobin, carboxyhemoglobin, and methemoglobin concentrations) or the absolute value of the bilirubin concentration in blood, without invading tissue.

A blood-constituent concentration measuring instrument according to the present invention is constructed so that concentrations of the constituent parts of blood can be optically measured without invasion. The blood-constituent concentration measuring instrument comprises: light source means for emitting measuring light to a portion of a living organism including a blood vessel, the measuring light having a plurality of wavelength components different from one another; straight-advance light discrimination means for extracting a straight-advance light component or a scattered light component close thereto from the measuring light passed through the living organism; extinction-index change detection means for detecting an extinction index change in the straight-advance light component or the scattered light component extracted by the straight-advance light discrimination means; and calculation means for calculating concentrations of the constituent parts of blood, based on the extinction index change for each wavelength component of the measuring light.

In a preferred form of the present invention, the light source means emits measuring light which has a plurality of wavelength components corresponding in number to variables to be measured, the variables including a constituent part to be measured.

In another preferred form of the present invention, the straight-advance light discrimination means is constructed of an optical heterodyne interferometer that generates a beat signal representing only the straight-advance light component or the scattered light component. Also, the straight-advance light discrimination means may be constructed of a streak camera that detects the straight-advance light component or the scattered light component in such a manner that it is discriminated on a time axis from a scattered light component incident at a later time than the straight-advance light component or the scattered light component.

In still another preferred form of the present invention, the extinction-index change detection means detects the extinction index change caused by pulsation of an artery of the living organism. Furthermore, the extinction-index change detection means may calculate a difference between the maximum and minimum values of a signal that detected the straight-advance light component or the scattered light component, thereby detecting the extinction index change caused by pulsation of an artery of the living organism.

In a further preferred form of the present invention, when the variables include n variables, the calculation means solves n simultaneous Lambert-Beer equations to calculate the concentrations of the constituent parts of blood.

It is another object of the present invention to provide a method of measuring a blood-constituent concentration comprising steps of irradiating measuring light onto a portion of a living organism including a blood vessel, the measuring light having a plurality of wavelength components different from one another extracting a straight-advance light component or a scattered light component close thereto from said measuring light passed through said living organism, detecting an extinction index change in said straight-advance light component or the scattered light component extracted by said straight-advance light discrimination means, and calculating concentration of the constituent parts of blood, based on the extinction index change for each wavelength component of the measuring light.

FIG. 1 shows the basic constitution of a blood-constituent concentration measuring instrument in accordance with the present invention. It will hereinafter be described, with reference to FIG. 1, that the concentrations of the constituent parts of blood can be measured with a high degree of accuracy.

For instance, light source means 1, consisting of n light sources Q1~Qn and dichroic mirrors M, emits measuring light S to a living organism 2 with a blood vessel. The measuring light S consists of wavelength components corresponding in number to variables to be measured. Let the wavelengths of these components be $\lambda 1, \lambda 2, \lambda 3, \ldots,$ and $\lambda n$, respectively. Since the living organism 2 is a strong scattering medium, the measuring light S incident upon the living organism 2 is mostly scattered and the greater part thereof behaves as multiple scattered light. However, the straight-advance component still remains slightly and the intensity I of the straight-advance light is expressed by the following equation. Note that FIG. 2 schematically depicts how the aforementioned straight-advance light and scattered light occur.

$$I = I_0 \exp(\mu \cdot C \cdot L)$$

where $I_0$ = incident light intensity, $\mu$ = attenuation coefficient,

L = thickness of a sample,

C = concentration of the constituent part of blood which causes extinction to occur.

Straight-advance light discrimination means 3 discriminates only a straight-advance light component or a scattered light component close thereto (i.e., a scattered light component traveling along nearly the same optical path as the straight light component) from the light scattered by the living organism 2.

The living organism 2, as schematically shown in FIG. 3, can be roughly classified into tissue, a vein, and an artery. If light is incident upon the living organism 2, then absorption and scattering will take place in the tissue, the vein, and the artery. As a result, the incident light will be attenuated. As is generally known, the artery pulsates. Therefore, if the intensity of the emergent light is observed, a change in the extinction index corresponding to the pulsation can be monitored.

Extinction-index change detection means 4 detects an extinction index change in the straight-advance light component or a scattered light component close thereto, extracted by the straight-advance light discrimination means 3. The extinction indices during expansion and contraction of the artery are respectively expressed by the following equations:

$$\ln(1/I_0)_1 = \mu \cdot C \cdot L_1$$

$$\ln(1/I_0)_2 = \mu \cdot C \cdot L_2$$

in which $L_1$ = optical path length during expansion of the artery, $L_2$ = optical path length during contraction of the artery.

The extinction index change $\Delta A$ between during expansion of the artery and during the contraction is expressed as $$\Delta A = \mu \cdot C \cdot \Delta L.$$

This means only a change in the extinction index caused by arterial blood (i.e., the extinction index caused by tissue or a vein is not included). $\Delta L$ represents a change in the optical path length caused by pulsation of arterial blood.

For the wavelengths, n wavelengths $\lambda 1 \sim \lambda n$ were prepared so as to correspond to the total number of the concentrations $C_1 \sim C_{n-1}$ of constituent parts to be measured and $\Delta L$. Calculation means 5 solves n simultaneous Lambert-Beer equations based on the extinction index changes $\Delta A$ in the n wavelengths $\lambda 1 \sim \lambda n$ of the measuring light, thereby calculating the concentrations $C_1 \sim C_{n-1}$ of a portion to be measured and $\Delta L$.

$$\Delta A_{\lambda 1} = (\mu_{C1-\lambda 1} \cdot C_1 + \mu_{C2-\lambda 1} \cdot C_2 + \ldots + \mu_{Cn-1-\lambda 1} \cdot C_{n-1}) \cdot \Delta L$$

$$\Delta A_{\lambda 2} = (\mu_{C1-\lambda 2} \cdot C_1 + \mu_{C2-\lambda 2} \cdot C_2 + \ldots + \mu_{Cn-2-\lambda 1} \cdot C_{n-1}) \cdot \Delta L$$

$$\Delta A_{\lambda n} = (\mu_{C1-\lambda n} \cdot C_1 + \mu_{C2-\lambda n} \cdot C_2 + \ldots + \mu_{Cn-1-\lambda n} \cdot C_{n-1}) \cdot \Delta L$$

As described above, the present invention can accurately measure the absolute values (contents) of the concentrations $C_1 \sim C_{n-1}$ of (n−1) constituent parts of blood without invading tissue. Even in the case where a measurement of an absolute value is not made, it becomes possible to measure constituent concentrations over a wide range with a high degree of accuracy.

BRIEF DESCRIPTION OF THE DRAWINGS

The above and other objects and advantages will become apparent from the following detailed description when read in conjunction with the accompanying drawings wherein:

FIG. 9 is a graph showing the absorption index characteristic of bilirubin;

FIG. 10 is a block diagram showing a blood-constituent concentration measuring instrument in accordance with a third embodiment of the present invention; and FIGS. 11 (A)–(B) are schematic diagrams used for explaining the discrimination of straight-advance light in the instrument shown in FIG. 10

DETAILED DESCRIPTION OF THE PREFERRED EMBODIMENTS

Figure 1:
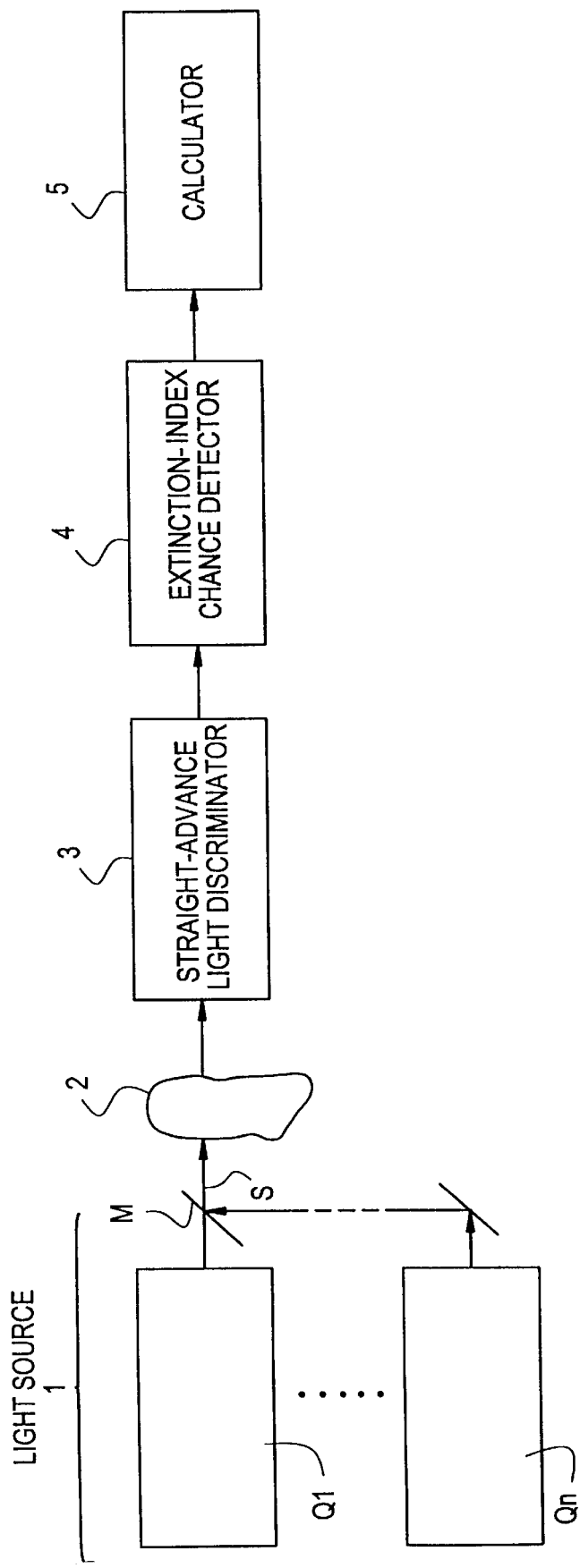
FIG. 1 is a block diagram showing the basic constitution of a blood-constituent concentration measuring instrument in accordance with the present invention.
Figure 2:
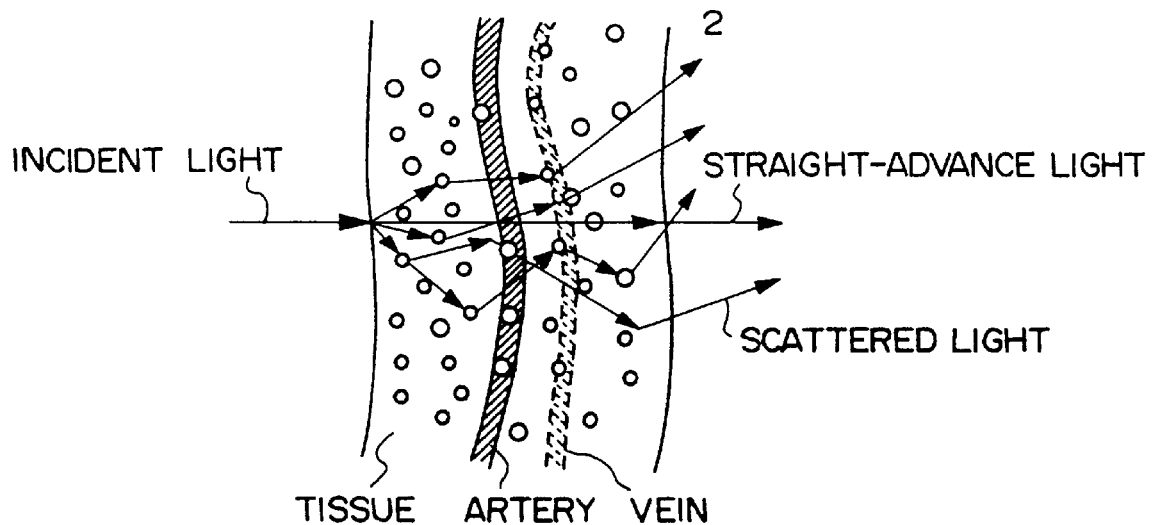
FIG. 2 is a schematic diagram used to explain the straight advance and scattering of light in a living organism.
Figure 3:
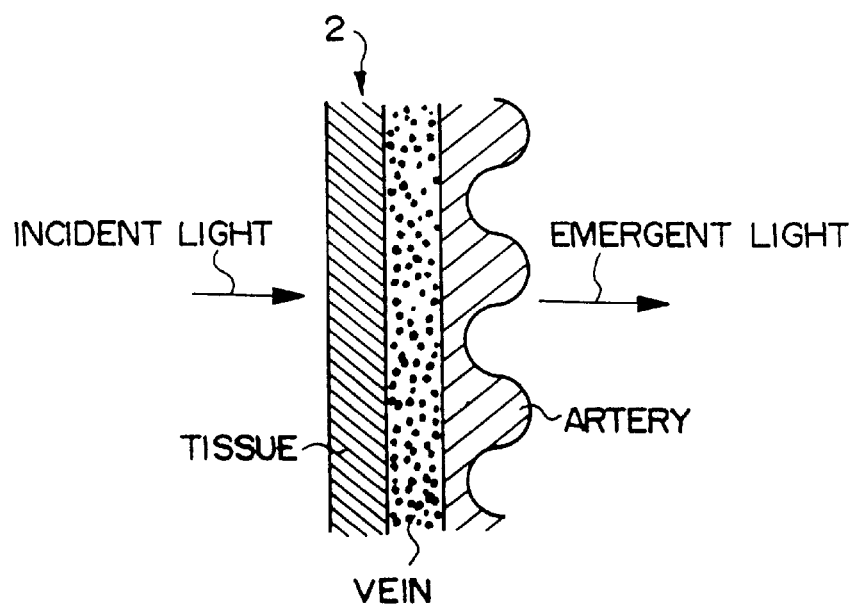
FIG. 3 is a schematic diagram used for explaining a change in the optical path length of straight-advance light traveling through a living organism, caused by pulsation of the artery.
Figure 4:
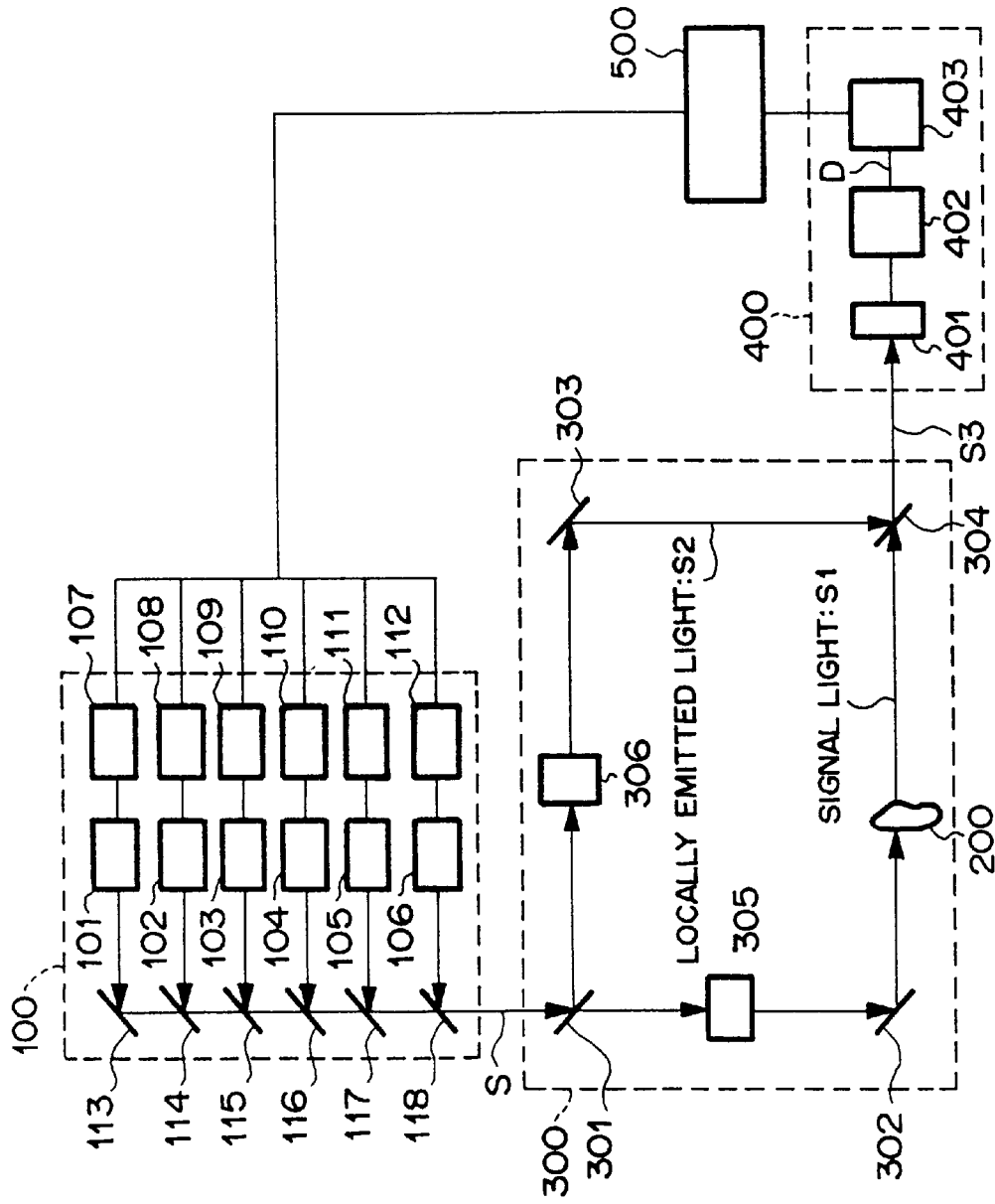
FIG. 4 is a block diagram showing a blood-constituent concentration measuring instrument in accordance with a first embodiment of the present invention.

Referring to FIG. 4, there is shown a blood-constituent concentration measuring instrument in accordance with a first embodiment of the present invention. This concentration measuring instrument is constructed to measure various hemoglobin concentrations (contents) in arterial blood. In FIG. 4, the concentration measuring instrument has light source means 100, a sample 200 to be measured (which is part of a human body and referred to as simply a sample 200), straight-advance light discrimination means 300, extinction-index change detection means 400, and calculation means 500.

Note that the variables to be measured in this embodiment include a hematocrit value, oxyhemoglobin concentration, deoxyhemoglobin concentration, carboxyhemoglobin concentration, methemoglobin concentration, and an optical path length change $\Delta L$.

Figure 5:
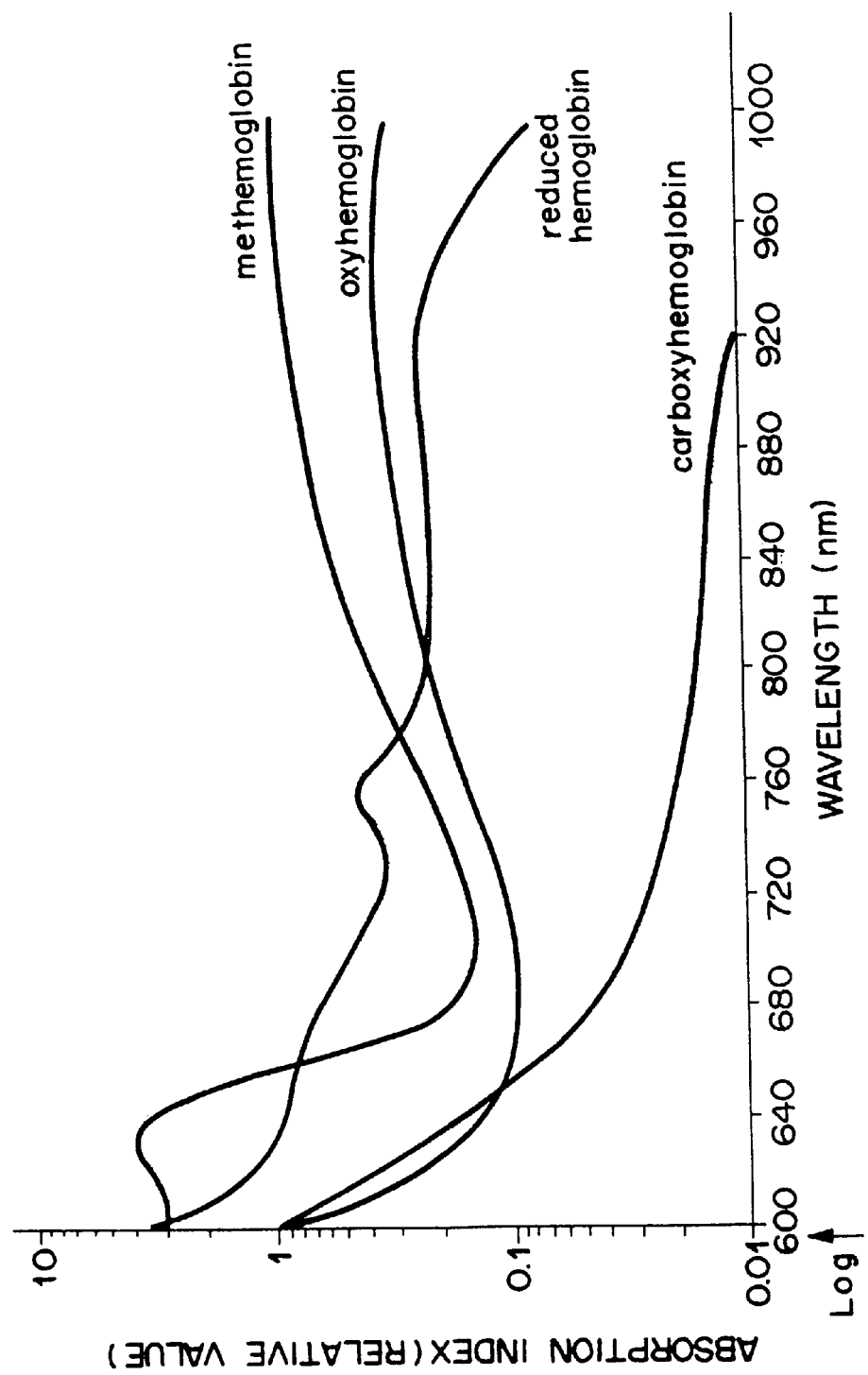
FIG. 5 is a graph showing the relationship between the wavelength and absorption index of emitted light for each of the constituent parts of blood.

The light source means 100 consists, for example, of 6 light sources 101~106, drivers 107~112, are reflecting mirror 113, and dichroic mirrors 114~118 corresponding to the light sources. As shown in FIG. 5, oxyhemoglobin, deoxyhemoglobin, carboxyhemoglobin, and methemoglobin vary in absorption index, depending upon measured wavelengths. Hence, as the light sources 101~106, light sources that emit light of wavelengths 660 nm, 790 nm, 805 nm, 830 nm, 850 nm, and 890 nm are respectively employed.

As the sample 200, part of a human body through which light is easily transmitted, for example, a thin portion such as an earlobe is selected.

The straight-advance discrimination means 300 employs an optical heterodyne interferometer. This optical heterodyne interferometer 300 consists of half mirrors 301 and 304, mirrors 302 and 303, and frequency shifters 305 and 306. As the frequency shifters 305 and 306, AOMs are employed. The frequency shifters 305 and 306 impart frequency shifts of 90 MHz and 89.9 MHz to measuring light S incident upon the shifters.

If the signal light S1 being transmitted through the sample 200 via the first frequency shifter 305 and the locally emitted light S2 via the second frequency shifter 306 are superposed by the half mirror 304, light S3 carrying a beat signal (the difference between the above-mentioned frequencies) will be obtained. If this beat signal is detected, only the straight-advance light component emitted from the sample 200 will be extracted. Thus, the straight-advance light discrimination means 300 discriminates straight-advance light.

Figure 6:
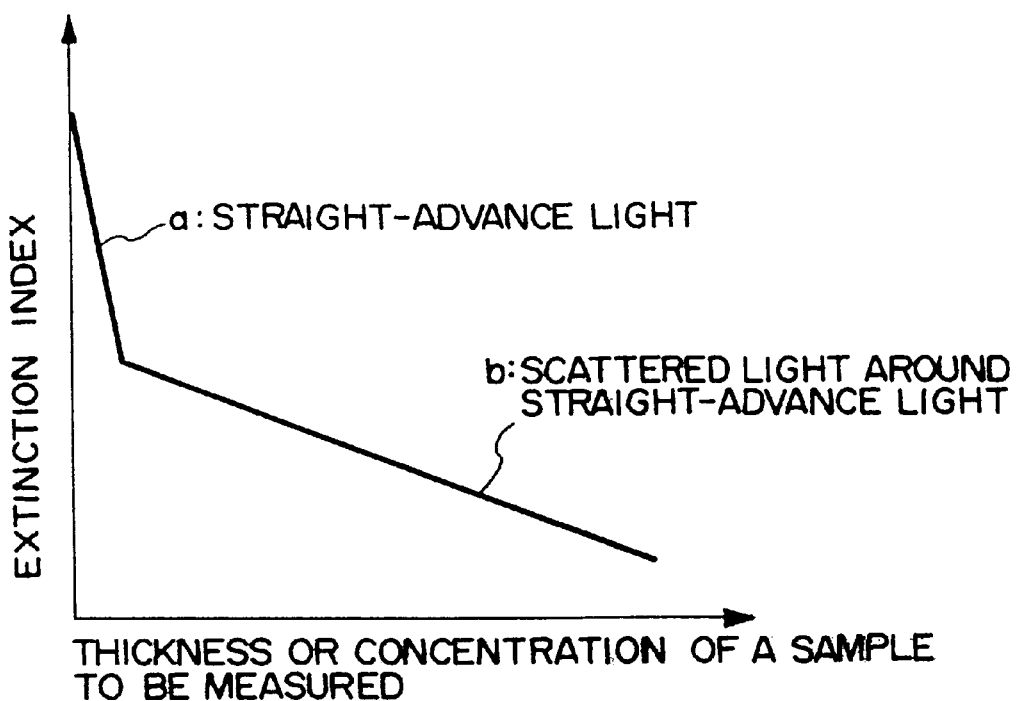
FIG. 6 is a graph used to explain the relationship between the degree of scattering and the extinction index of light transmitted through a living organism.

If the aforementioned straight-advance light is detected, the optical path length will become constant regardless of the wavelength of the measuring light. Note that in the case where scattering on the sample 200 is significantly great, straight-advance light will be buried in multiple scattered light. However, even in this case, the optical path length can be considered approximately constant independent of the wavelength of the measuring light, by extracting apparent straight-advance light (i.e., scattered light that travels along a very similar optical path as a straight-advance light component). FIG. 6 shows the rough relationship between the thickness or concentration of a sample to be measured and an extinction index. In the figure, reference characters a and b represent straight-advance light and apparent straight-advance light, respectively. Since the extinction index of this apparent straight-advance light is linear in the same way as true straight-advance light, it can be handled in the same way as straight-advance light.

Figure 7:
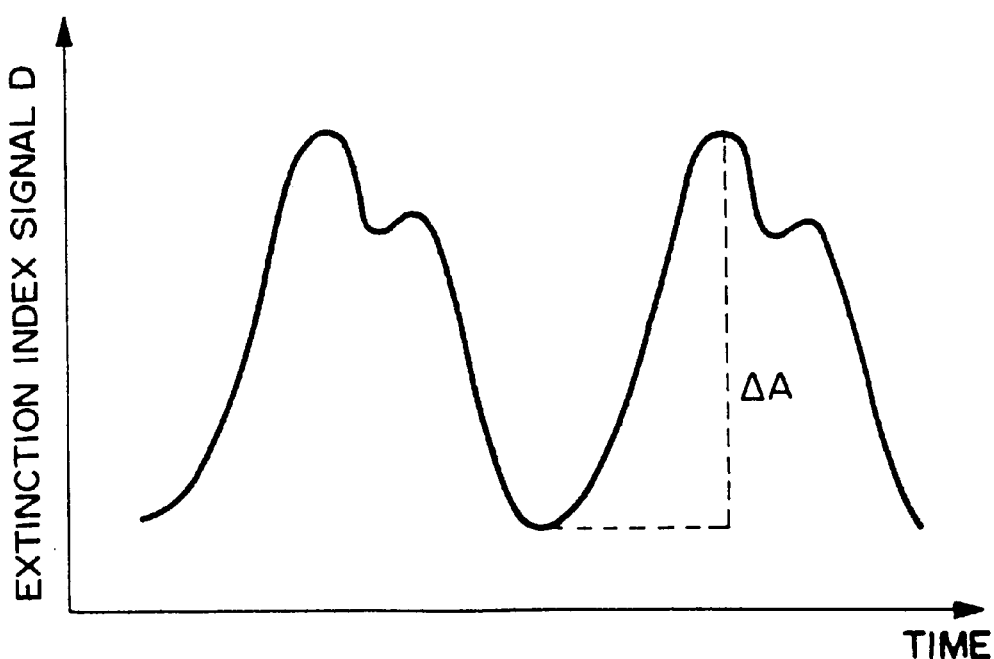
FIG. 7 is a graph used for explaining an extinction index change represented by the detection signal of the straight-advance light transmitted through the living organism.

The extinction-index change detection means 400 consists of an optical detector 401, an amplifier 402, and an AD converter 403 that is serially driven. The optical detector 401 detects the light of respective wavelengths emitted by the light sources 101~106, and the aforementioned beat signal contained in the output is amplified by the amplifier 402 and is obtained as an extinction-index signal D. As shown in FIG. 7, the maximum and minimum values of each pulsating extinction-index signal D are sampled by the AD converter 403, and the difference therebetween, i.e., extinction index change $\Delta A$ is calculated for each above-mentioned wavelength.

The calculation means 500 uses oxyhemoglobin concentration (content) Coxy, deoxyhemoglobin concentration (content) Cdeoxy, carboxyhemoglobin concentration (content) Cco, methemoglobin concentration (content) Cmet, an optical path length change $\Delta L$, and a hematocrit value hem as variables to be measured, and solves the following 6 simultaneous Lambert-Beer equations corresponding to 6 wavelengths, thereby calculating Coxy, Cdeoxy, Cco, and Cmet.

$$\Delta A\lambda 1 = \text{hem} \cdot (\mu\text{oxy}-\lambda 1 \cdot \text{Coxy} + \mu\text{deoxy}-\lambda 1 \cdot \text{Cdeoxy} + \mu\text{co}-\lambda 1 \cdot \text{Cco} + \mu\text{met}-\lambda 1 \cdot \text{Cmet}) \cdot \Delta L$$

$$\Delta A\lambda 2 = \text{hem} \cdot (\mu\text{oxy}-\lambda 2 \cdot \text{Coxy} + \mu\text{deoxy}-\lambda 2 \cdot \text{Cdeoxy} + \mu\text{co}-\lambda 2 \cdot \text{Cco} + \mu\text{met}-\lambda 2 \cdot \text{Cmet}) \cdot \Delta L$$

$$\Delta A\lambda 3 = \text{hem} \cdot (\mu\text{oxy}-\lambda 3 \cdot \text{Coxy} + \mu\text{deoxy}-\lambda 3 \cdot \text{Cdeoxy} + \mu\text{co}-\lambda 3 \cdot \text{Cco} + \mu\text{met}-\lambda 3 \cdot \text{Cmet}) \cdot \Delta L$$

$$\Delta A\lambda 4 = \text{hem} \cdot (\mu\text{oxy}-\lambda 4 \cdot \text{Coxy} + \mu\text{deoxy}-\lambda 4 \cdot \text{Cdeoxy} + \mu\text{co}-\lambda 4 \cdot \text{Cco} + \mu\text{met}-\lambda 4 \cdot \text{Cmet}) \cdot \Delta L$$

$$\Delta A\lambda 5 = \text{hem} \cdot (\mu\text{oxy}-\lambda 5 \cdot \text{Coxy} + \mu\text{deoxy}-\lambda 5 \cdot \text{Cdeoxy} + \mu\text{co}-\lambda 5 \cdot \text{Cco} + \mu\text{met}-\lambda 5 \cdot \text{Cmet}) \cdot \Delta L$$

$$\Delta A\lambda 6 = \text{hem} \cdot (\mu\text{oxy}-\lambda 6 \cdot \text{Coxy} + \mu\text{deoxy}-\lambda 6 \cdot \text{Cdeoxy} + \mu\text{co}-\lambda 6 \cdot \text{Cco} + \mu\text{met}-\lambda 6 \cdot \text{Cmet}) \cdot \Delta L$$

where $\Delta A\lambda 1$=extinction index change in a light source wavelength of $\lambda 1$=660 nm, $\Delta A\lambda 2$=extinction index change in a light source wavelength of $\lambda 2$=790 nm, $\Delta A\lambda 3$=extinction index change in a light source wavelength of $\lambda 3$=805 nm, $\Delta A\lambda 4$=extinction index change in a light source wavelength of $\lambda 4$=830 nm, $\Delta A\lambda 5$=extinction index change in a light source wavelength of $\lambda 5$=850 nm, $\Delta A\lambda 6$=extinction index change in a light source wavelength of $\lambda 6$=890 nm, and these values are calculated as described above, and where $\mu\text{oxy}-\lambda 1$=attenuation coefficient of oxyhemoglobin in a light source wavelength of $\lambda 1$=660 nm, $\mu\text{oxy}-\lambda 2$=attenuation coefficient of oxyhemoglobin in a light source wavelength of $\lambda 2$=790 nm, $\mu\text{oxy}-\lambda 3$=attenuation coefficient of oxyhemoglobin in a light source wavelength of $\lambda 3$=805 nm, $\mu\text{oxy}-\lambda 4$=attenuation coefficient of oxyhemoglobin in a light source wavelength of $\lambda 4$=830 nm, $\mu\text{oxy}-\lambda 5$=attenuation coefficient of oxyhemoglobin in a light source wavelength of $\lambda 5$=850 nm, $\mu\text{oxy}-\lambda 6$=attenuation coefficient of oxyhemoglobin in a light source wavelength of $\lambda 6$=890 nm, $\mu\text{deoxy}-\lambda 1$=attenuation coefficient of deoxyhemoglobin in a light source wavelength of $\lambda 1$=660 nm, $\mu\text{deoxy}-\lambda 2$=attenuation coefficient of deoxyhemoglobin in a light source wavelength of $\lambda 2$=790 nm, $\mu\text{deoxy}-\lambda 3$=attenuation coefficient of deoxyhemoglobin in a light source wavelength of $\lambda 3$=805nm, $\mu\text{deoxy}-\lambda 4$=attenuation coefficient of deoxyhemoglobin in a light source wavelength of $\lambda 4$=830 nm, $\mu\text{deoxy}-\lambda 5$=attenuation coefficient of deoxyhemoglobin in a light source wavelength of $\lambda 5$=850 nm, $\mu\text{deoxy}-\lambda 6$=attenuation coefficient of deoxyhemoglobin in a light source wavelength of $\lambda 6$=890 nm, $\mu\text{co}-\mu 1$=attenuation coefficient of carboxyhemoglobin in a light source wavelength of $\lambda 1$=660 nm, $\mu\text{co}-\mu 2$=attenuation coefficient of carboxyhemoglobin in a light source wavelength of $\lambda 2$=790 nm, $\mu\text{co}-\mu 3$=attenuation coefficient of carboxyhemoglobin in a light source wavelength of $\lambda 3$=805 nm, $\mu\text{co}-\mu 4$=attenuation coefficient of carboxyhemoglobin in a light source wavelength of $\lambda 4$=830 nm, $\mu\text{co}-\lambda 5$=attenuation coefficient of carboxyhemoglobin in a light source wavelength of $\lambda 5$=850 nm, $\mu\text{co}-\lambda 6$=attenuation coefficient of carboxyhemoglobin in a light source wavelength of $\lambda 6$=890 nm, $\mu\text{met}-\lambda 1$=attenuation coefficient of methemoglobin in a light source wavelength of $\lambda 1$=660 nm, $\mu\text{met}-\lambda 2$=attenuation coefficient of methemoglobin in a light source wavelength of $\lambda 2$=790 nm, $\mu\text{met}-\lambda 3$=attenuation coefficient of methemoglobin in a light source wavelength of $\lambda 3$=805 nm, $\mu\text{met}-\lambda 4$=attenuation coefficient of methemoglobin in a light source wavelength of $\lambda 4$=830 nm, $\mu\text{met}-\lambda 5$=attenuation coefficient of methemoglobin in a light source wavelength of $\lambda 5$=850 nm, $\mu\text{met}-\lambda 6$=attenuation coefficient of methemoglobin in a light source wavelength of $\lambda 6$=890 nm, and these values have previously been prepared.

Note that the degree of oxygen saturation, $SpO_2$, can be calculated by the following equation:

$$SpO_2 = [Coxy/(Coxy+Cdeoxy+Cco+Cmet)].$$

According to the first embodiment, as described above, the contents of oxyhemoglobin deoxyhemoglobin, carboxyhemoglobin, and methemoglobin, and the degree of oxygen saturation can be calculated. Since the hematocrit value is also contained in the variables to be measured, there is no possibility of the measurement accuracy in the degree of oxygen saturation being degraded by different hemotocrit values.

Figure 8:
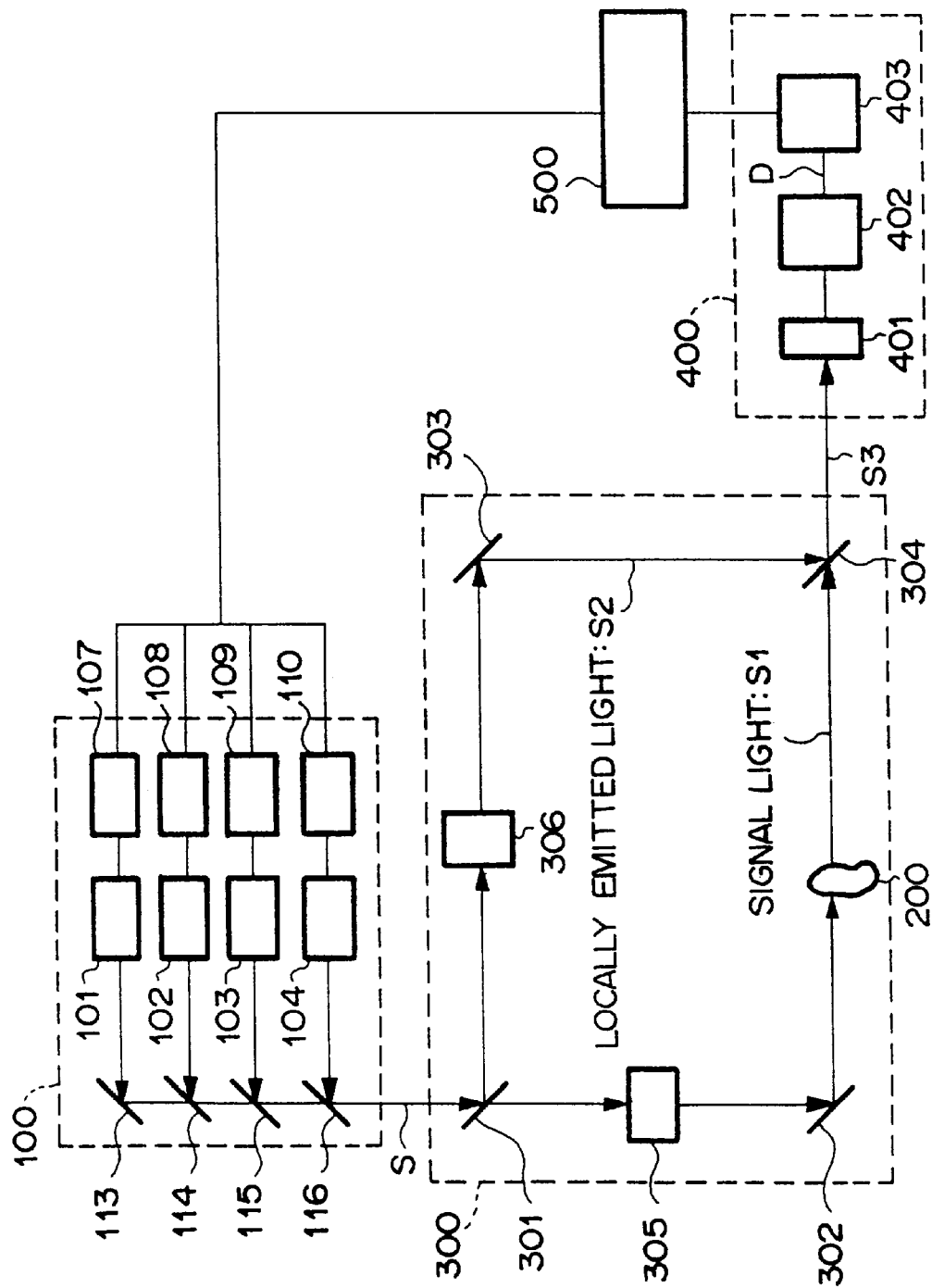
FIG. 8 is a block diagram showing a blood-constituent concentration measuring instrument in accordance with a second embodiment of the present invention.

FIG. 8 illustrates a blood-constituent concentration measuring instrument in accordance with a second embodiment of the present invention. This concentration measuring instrument is intended for newborn babies and constructed to measure the bilirubin concentration (content) in arterial blood. The same reference numerals will be applied to the same parts as the first embodiment for omitting a detailed description thereof. In FIG. 8, the concentration measuring instrument has light source means 100, a sample 200 (which is part of a human body), straight-advance light discrimination means 300, extinction-index change detection means 400, and calculation means 500.

Note that the variables to be measured in the second embodiment include the bilirubin concentration, oxyhemoglobin concentration, and deoxyhemoglobin concentration in the arterial blood of a newborn baby, and an optical path length change $\Delta L$.

The light source means 100 consists, for example, of 4 light sources 101~104, drivers 107~110, a reflecting mirror 113, and dichroic mirrors 114~116 corresponding to the light sources. As illustrated in FIG. 9, the bilirubin has a large absorption band between a wavelength of 450 nm and a wavelength of 470 nm. Hence, as the light source 101, one that emits light of wavelength 473 nm is employed. As the light sources 102~104, those that emit light of wavelengths 660 nm, 790 nm, and 830 nm are respectively employed.

As the sample 200, part of a human body through which light is easily transmitted, for example, a thin portion such as an earlobe is selected.

As the straight-advance discrimination means 300, an optical heterodyne interferometer is employed. This optical heterodyne interferometer 300 consists of half mirrors 301 and 304, mirrors 302 and 303, and frequency shifters 305 and 306. As the frequency shifters 305 and 306, AOMs are employed. The frequency shifters 305 and 306 impart frequency shifts of 90 MHz and 89.9 MHz to measuring light S incident upon the shifters.

If the signal light S1 being transmitted through the sample 200 via the first frequency shifter 305 and the locally emitted light S2 via the second frequency shifter 306 are superposed by the half mirror 304, light S3 carrying a beat signal (the difference between the above-mentioned frequencies) will be obtained.

The extinction-index change detection means 400 consists of an optical detector 401, an amplifier 402, and an AD converter 403 that is serially driven. The optical detector 401 detects the light of respective wavelengths emitted by the light sources 101~104, and the aforementioned beat signal contained in the output is amplified by the amplifier 402 and is obtained as an extinction-index signal D. As illustrated in FIG. 7, the maximum and minimum values of each pulsating extinction-index signal D are sampled by the AD converter 403, and the difference therebetween, i.e., extinction index change $\Delta A$, is calculated for each above-mentioned wavelength.

The calculation means 500 uses bilirubin concentration (content) Cbil, oxyhemoglobin concentration (content) Coxy, and deoxyhemoglobin concentration (content) Cdeoxy, and an optical path length change $\Delta L$ as variables to be measured, and solves the following 4 simultaneous Lambert-Beer equations corresponding to 4 wavelengths, thereby calculating Cbil, Coxy, and Cdeoxy.

$$\Delta A\lambda 1 = \text{hem} \cdot (\mu\text{oxy-}\lambda 1 \cdot \text{Coxy} + \mu\text{deoxy-}\lambda 1 \cdot \text{Cdeoxy}) \cdot \Delta L + \mu\text{bil-}\lambda 1 \cdot \text{Cbil} \cdot \Delta L$$

$$\Delta A\lambda 2 = \text{hem} \cdot (\mu\text{oxy-}\lambda 2 \cdot \text{Coxy} + \mu\text{deoxy-}\lambda 2 \cdot \text{Cdeoxy}) \cdot \Delta L + \mu\text{bil-}\lambda 2 \cdot \text{Cbil} \cdot \Delta L$$

$$\Delta A\lambda 3 = \text{hem} \cdot (\mu\text{oxy-}\lambda 3 \cdot \text{Coxy} + \mu\text{deoxy-}\lambda 3 \cdot \text{Cdeoxy}) \cdot \Delta L + \mu\text{bil-}\lambda 3 \cdot \text{Cbil} \cdot \Delta L$$

$$\Delta A\lambda 4 = \text{hem} \cdot (\mu\text{oxy-}\lambda 4 \cdot \text{Coxy} + \mu\text{deoxy-}\lambda 4 \cdot \text{Cdeoxy}) \cdot \Delta L + \mu\text{bil-}\lambda 4 \cdot \text{Cbil} \cdot \Delta L$$

in which
  $\Delta A\lambda 1$=extinction index change in a light source wavelength of $\lambda 1$=473 nm,
  $\Delta A\lambda 2$=extinction index change in a light source wavelength of $\lambda 2$=660 nm,
  $\Delta A\lambda 3$=extinction index change in a light source wavelength of $\lambda 3$=790 nm,
  $\Delta A\lambda 4$=extinction index change in a light source wavelength of $\lambda 4$=830 nm,
and these values are calculated as described above, and in which
  $\mu$oxy-$\lambda 1$=attenuation coefficient of oxyhemoglobin in a light source wavelength of $\lambda 1$=473 nm,
  $\mu$oxy-$\lambda 2$=attenuation coefficient of oxyhemoglobin in a light source wavelength of $\lambda 2$=660 nm,
  $\mu$oxy-$\lambda 3$=attenuation coefficient of oxyhemoglobin in a light source wavelength of $\lambda 3$=790 nm,
  $\mu$oxy-$\lambda 4$=attenuation coefficient of oxyhemoglobin in a light source wavelength of $\lambda 4$=830 nm,
  $\mu$deoxy-$\lambda 1$=attenuation coefficient of deoxyhemoglobin in a light source wavelength of $\lambda 1$=473 nm,
  $\mu$deoxy-$\lambda 2$=attenuation coefficient of deoxyhemoglobin in a light source wavelength of $\lambda 2$=660 nm,
  $\mu$deoxy-$\lambda 3$=attenuation coefficient of deoxyhemoglobin in a light source wavelength of $\lambda 3$=790 nm,
  $\mu$deoxy-$\lambda 4$=attenuation coefficient of deoxyhemoglobin in a light source wavelength of $\lambda 4$=830 nm,
  $\mu$bil-1=attenuation coefficient of bilirubin in a light source wavelength of $\lambda 1$=473 nm,
  $\mu$bil-2=attenuation coefficient of bilirubin in a light source wavelength of $\lambda 2$=660 nm,
  $\mu$bil-3=attenuation coefficient of bilirubin in a light source wavelength of $\lambda 3$=790 nm,
  $\mu$bil-4=attenuation coefficient of bilirubin in a light source wavelength of $\lambda 4$=830 nm,
  hem=typical hemotocrit value in a person,
and these values have previously been prepared.

FIG. 10 shows a blood-constituent concentration measuring instrument in accordance with a third embodiment of the present invention. This concentration measuring instrument is constructed to measure in a wide range the relative concentrations of the oxyhemoglobin, deoxyhemoglobin, carboxyhemoglobin, and methemoglobin in blood. The same reference numerals will be applied to the same parts as the first embodiment for omitting a detailed description thereof. In FIG. 10, the concentration measuring instrument has light source means 150, a sample 200 (which is part of a human body), straight-advance light discrimination means 350, extinction-index change detection means 450, and calculation means 500.

The light source means 150 consists of 4 picosecond light sources 151~154 for emitting light in a very short time width in the order of a picosecond, and light source drivers 161~164 corresponding to the light sources. Note that, as the light sources 151~154, those that emit light of wavelengths 780 nm, 805 nm, 830 nm, and 850 nm are respectively employed.

As the sample 200, part of a human body through which light is easily transmitted, for example, a thin portion such as an earlobe, is selected.

As the straight-advance discrimination means 350, a streak camera capable of detecting with high time resolution the intensity of incident light is employed. Since the picosecond light sources 151~154 and this streak camera 350 form a time gate, the straight-advance light component or a component close to the straight-advance light component, emitted from the sample 200, can be extracted.

The above-mentioned extraction is depicted in FIG. 11. That is, while the intensity I(t) of the light emitted from the picosecond light sources 151~154 shows a sharp time change such as that shown in FIG. 11A, the streak camera 350 detects straight-advance light and also scattered light incident at a later time than that light. Therefore, the time change in the intensity i' (t) of the light detected by the streak camera 350 becomes one such as FIG. 11B. Hence, if the streak camera 350 detects the detected light intensity I' (t) at time T1' that has elapsed since the start time T1 of the change by a short time, the intensity of straight-advance light alone can be detected.

On the other hand, the extinction-index change detection means 450 is constructed of an AD converter 403, which is serially driven. The maximum and minimum values of each pulsating extinction-index signal D are sampled by the AD converter 403, and the difference therebetween, i.e., extinction index change $\Delta A$ is calculated for each of the above-mentioned wavelengths emitted by the light sources 151~154.

The calculation means 500 solves the following 4 simultaneous Lambert-Beer equations corresponding to 4 wavelengths with oxyhemoglobin, deoxyhemoglobin, carboxyhemoglobin, and methemoglobin concentrations as variables to be measured.

$$\Delta A \lambda 1 = hem \cdot (\mu oxy-\lambda 1 \cdot Coxy + \mu deoxy-\lambda 1 \cdot Cdeoxy + \mu co-\lambda 1 \cdot Cco + \mu met-\lambda 1 \cdot Cmet) \cdot \Delta L$$

$$\Delta A \lambda 2 = hem \cdot (\mu oxy-\lambda 2 \cdot Coxy + \mu deoxy-\lambda 2 \cdot Cdeoxy + \mu co-\lambda 2 \cdot Cco + \mu met-\lambda 2 \cdot Cmet) \cdot \Delta L$$

$$\Delta A \lambda 3 = hem \cdot (\mu oxy-\lambda 3 \cdot Coxy + \mu deoxy-\lambda 3 \cdot Cdeoxy + \mu co-\lambda 3 \cdot Cco + \mu met-\lambda 3 \cdot Cmet) \cdot \Delta L$$

$$\Delta A \lambda 4 = hem \cdot (\mu oxy-\lambda 4 \cdot Coxy + \mu deoxy-\lambda 4 \cdot Cdeoxy + \mu co-\lambda 4 \cdot Cco + \mu met-\lambda 4 \cdot Cmet) \cdot \Delta L$$

From the above-mentioned equations, $$\Delta A \lambda 2 / \Delta A \lambda 1 = (\mu oxy-\lambda 2 \cdot Coxy + \mu deoxy-\lambda 2 \cdot Cdeoxy + \mu co-\lambda 2 \cdot Cco + \mu met-\lambda 2 \cdot Cmet)/(\mu oxy-\lambda 1 \cdot Coxy + \mu deoxy-\lambda 1 \cdot Cdeoxy + \mu co-\lambda 1 \cdot Cco + \mu met-\lambda 1 \cdot Cmet) \cdot \Delta L$$

$$\Delta A \lambda 3 / \Delta A \lambda 1 = (\mu oxy-\lambda 3 \cdot Coxy + \mu deoxy-\lambda 3 \cdot Cdeoxy + \mu co-\lambda 3 \cdot Cco + \mu met-\lambda 3 \cdot Cmet)/(\mu oxy-\lambda 1 \cdot Coxy + \mu deoxy-\lambda 1 \cdot Cdeoxy + \mu co-\lambda 1 \cdot Cco + \mu met-\lambda 1 \cdot Cmet) \cdot \Delta L$$

$$\Delta A \lambda 4 / \Delta A \lambda 1 = (\mu oxy-\lambda 4 \cdot Coxy + \mu deoxy-\lambda 4 \cdot Cdeoxy + \mu co-\lambda 4 \cdot Cco + \mu met-\lambda 4 \cdot Cmet)/(\mu oxy-\lambda 1 \cdot Coxy + \mu deoxy-\lambda 1 \cdot Cdeoxy + \mu co-\lambda 1 \cdot Cco + \mu met-\lambda 1 \cdot Cmet) \cdot \Delta L$$

From Coxy+Cdeoxy+Cmet=100, $$SpO_2 = [Coxy/(Coxy+Cdeoxy+Cco+Cmet)].$$

Furthermore, the relative concentrations of various kinds of hemoglobin can be measured.

While the present invention has been described with reference to the preferred embodiments thereof, the invention is not to be limited to the details given herein, but may be modified within the scope of the appended claims.

What is claimed is:

1. A blood-constituent concentration measuring instrument comprising:

light source means for emitting measuring light to a portion of a living organism including a blood vessel, the measuring light having a plurality of wavelength components different from one another;

straight-advance light discrimination means for extracting a straight-advance light component or a scattered light component traveling along nearly a same optical path as said straight-advance light component from said measuring light which has passed through said living organism;

extinction-index change detection means for detecting an extinction index change in said straight-advance light component or said scattered light component extracted by said straight-advance light discrimination means; and calculation means for calculating concentrations of the constituent parts of the blood, based on said extinction index change for each wavelength component of said measuring light.

2. The blood-constituent concentration measuring instrument as set forth in claim 1, wherein said light source means emits measuring light which has a plurality of wavelength components corresponding in number to variables to be measured, the variables corresponding to the constituent parts of blood to be measured.

3. The blood-constituent concentration measuring instrument as set forth in claim 2, wherein said straight-advance light discrimination means is constructed of an optical heterodyne interferometer that generates a beat signal representing only said straight-advance light component or said scattered light component.

4. The blood-constituent concentration measuring instrument as set forth in claim 2, wherein said straight-advance light discrimination means is constructed of a streak camera that detects said straight-advance light component or said scattered light component in such a manner that it is discriminated on a time axis from a scattered light component incident at a later time than said straight-advance light component or said scattered light component.

5. The blood-constituent concentration measuring instrument as set forth in claim 2, wherein, when said variables include n variables, said calculation means solves n simultaneous Lambert-Beer equations to calculate the concentrations of said constituent parts of blood.

6. The blood-constituent concentration measuring instrument as set forth in claim 2, wherein said variables include a hematocrit value and said calculation means performs said calculation.

7. The blood-constituent concentration measuring instrument as set forth in claim 1, wherein said straight-advance light discrimination means is constructed of an optical heterodyne interferometer that generates a beat signal representing only said straight-advance light component or said scattered light component.

8. The blood-constituent concentration measuring instrument as set forth in claim 1, wherein said straight-advance light discrimination means is constructed of a streak camera that detects said straight-advance light component or said scattered light component in such a manner that it is discriminated on a time axis from a scattered light component incident at a later time than said straight-advance light component or said scattered light component.

9. The blood-constituent concentration measuring instrument as set forth in any one of claims 1 through 4, wherein said extinction-index change detection means detects said extinction index change caused by pulsation of an artery of said living organism.

10. The blood-constituent concentration measuring instrument as set forth in claim 1, wherein said extinction-index change detection means calculates a difference between the maximum and minimum values of a signal that was obtained by detecting said straight-advance light component or said scattered light component, thereby detecting said extinction index change caused by pulsation of an artery of said living organism.

11. A method of measuring blood-constituent concentrations comprising steps of:

irradiating measuring light onto a portion of a living organism including a blood vessel, the measuring light having a plurality of wavelength components different from one another;

extracting a straight-advance light component or a scattered light component traveling along nearly a same optical path as said straight-advance light component from said measuring light which has passed through said living organism;

detecting an extinction index change in said straight-advance light component or said scattered light component extracted in said extracting step; and calculating the concentrations of the constituent parts of the blood, based on said extinction index change for each wavelength component of said measuring light.

* * * * *